United States Patent [19]
Skinner et al.

[11] Patent Number: 5,749,729
[45] Date of Patent: May 12, 1998

[54] DENTAL ABSORBENCY DEVICE

[76] Inventors: Gregory C. Skinner, 250 S. Lyon Ave., Hemet, Calif. 92543; Gaylen J. Cox, 129 W. Parkway, Provo, Utah 84604

[21] Appl. No.: 757,387

[22] Filed: Nov. 27, 1996

[51] Int. Cl.$^6$ ...................................................... A61C 5/14
[52] U.S. Cl. ................................... 433/136; 604/385.1
[58] Field of Search ........................... 433/136, 140; 604/385.1

[56] References Cited

U.S. PATENT DOCUMENTS

| | | | |
|---|---|---|---|
| 2,613,441 | 10/1952 | Biggs | 32/34 |
| 3,468,030 | 9/1969 | Peyser et al. | 32/34 |
| 4,293,301 | 10/1981 | Mattsson | 433/136 |
| 4,344,758 | 8/1982 | Wielhouwer et al. | 433/136 |
| 4,372,314 | 2/1983 | Wall | 128/296 |
| 4,501,586 | 2/1985 | Holtman | 604/380 |
| 4,657,539 | 4/1987 | Hasse | 604/385 |
| 4,705,514 | 11/1987 | Barnard | 604/383 |
| 4,813,872 | 3/1989 | Knitter | 433/136 |
| 4,826,433 | 5/1989 | Sakai et al. | 433/136 |
| 4,834,739 | 5/1989 | Linker, III et al. | 604/385.1 |
| 4,950,264 | 8/1990 | Osborn, III | 604/385.1 |
| 5,071,349 | 12/1991 | Skinner | 433/136 |

FOREIGN PATENT DOCUMENTS

| | | | |
|---|---|---|---|
| 646560 | 5/1937 | Germany | 433/136 |

*Primary Examiner*—John J. Wilson
*Attorney, Agent, or Firm*—Madson & Metcalf

[57] ABSTRACT

A dental absorbency device is disclosed in one presently preferred embodiment of the present invention as including a flat section comprising a single sheet of a highly absorbent material having a contoured elongated shape preferably sized to fit comfortably within a human mouth for the purpose of absorbing moisture, contaminants, blood, saliva, water, and/or other fluids at an operative field. In preferred design, the flat section may be formed having an upper surface, a lower surface, and peripheral edges which are unobstructed to fluid flow so as to provide a means for encouraging the absorption of fluids therethrough. The upper surface is preferably formed having an impervious, non-absorbent coating that resists slippage of the elongated flat section when disposed within the mouth of a patient. Structurally, the upper surface of the flat section includes at least one porous opening for absorbing fluids therethrough, whereas in contrast, the lower surface provides a means for absorbing fluids through its entire external surface area. A collection reservoir is preferably disposed between the upper and lower surfaces of the elongated flat section and functions to provide a means for retaining the collected fluids therein.

19 Claims, 2 Drawing Sheets

DENTAL ABSORBENCY DEVICE

RELATED APPLICATIONS

This application is a continuation-in-part of our provisional application Ser. No. 60/007,706, filed on Nov. 29, 1995 for the DENTAL ABSORBENCY DEVICE.

BACKGROUND

1. The Field of the Invention

This invention relates to absorption devices and, more particularly, to novel absorbency devices which can be used in cooperation with medical and/or dental procedures to provide a means for absorbing moisture, contaminants, debris, blood, saliva, water, and/or other liquids.

2. The Background Art

It has long been common for a dentist in the performance of a dental procedure to install a cotton-type sponge in the mouth of a patient to absorb liquid from an operative field or area where a dentist is conducting a procedure. Such sponges are generally comprised of a compressed roll of an absorbent cotton which may be positioned alongside, over or adjacent a patient's salivary ducts, against a patient's gingiva, and/or may be arranged next to an operative field.

Such cotton-roll-type sponges are generally intended to prohibit liquid from flowing or seeping into an operating field, which field is usually the surface of a patient's tooth or gingiva (gums). A roll-type sponge made from a stack of pads that are stitched together at their center longitudinal axis is shown in a patent to Julius, U.S. Pat. No. 4,071,955. A similar roll-type sponge is shown in a patent to Wall, U.S. Pat. No. 4,372,314 which essentially comprises a roll of alternating layers of gauze and non-woven material having a impervious encasing which isolates saliva in a patient's mouth away from an open wound to promote coagulation of the blood. In practice, it has been found that round rolls often float out of position, and interfere with a dental procedure being performed. Accordingly, it is difficult to position and maintain in a dental procedure within the close confines of a patient's mouth.

Other sponges that are configured for placement at certain locations in a patient's mouth for collection of liquids are shown in patents to Saffro, U.S. Pat. No. 3,705,585 and Biggs, U.S. Pat. No. 2,613,441. Which devices are formed to fit in or on certain locations, which are bulky and difficult to install, and are accordingly unlike the dental absorbency device of the present invention Like the present invention, certain prior art sponges have the value of a contoured and thin moisture absorbent device for use in the mouth of a dental patient. A patent to Peyser et al., U.S. Pat. No. 3,468,030 recognizes this need and provides a triangular arrangement that is essentially flat and intended to fit within a mouth cavity and which further comprises a thin layer of metal foil on the exposed surface which reflects available light. The shape of the Peyser et al. device, however, is unlike the present invention, and does not provide for an effective absorption of moisture nor does it adequately span a work area or operative field within the mouth of a patient. Further, the Peyser et al. device would not fit under a patient's tongue or in the areas adjacent thereto, nor will it fit appropriately in the front of a patient's mouth in the frenum area thereof. Additionally, the present invention lends itself to being folded longitudinally upon itself in order to fit within a narrow operative field or work area so as to be out of the way of the performance of the dentist conducting a dental procedure.

An earlier patent of one of the present inventors, U.S. Pat. No. 5,071,349, is directed to a mouth dam generally comprising an elongated flat section formed as a sandwich from at least two layers of an absorbent material. The two layers of absorbent material are cut or punched so as to compress the two layers together in such a manner to form a uniform seal around the peripheral edges of the mouth dam, thus defining an open area or reservoir disposed between the two sheets or layers of material. As a result of the sealed peripheral edges of the elongated flat section, the introduction of liquids or fluids into the open area or reservoir disposed between the two sheets or layers of absorption materials is inherently restricted to the passage of fluids or liquids through the upper and lower surfaces only thereby limiting the rate of absorption.

BRIEF SUMMARY AND OBJECTS OF THE INVENTION

In view of the foregoing, it is a primary object of the present invention to provide a novel dental absorbency device.

It is also an object of the present invention to provide a dental absorbency device which has a contoured elongated shape for fitting comfortably and conveniently within the mouth of a patient to provide a means for absorbing moisture, contaminants, blood, saliva, water, and/or other fluids from an operative field.

Further, it is an object of the present invention to provide a dental absorbency device which is formed of a single sheet of a flexible, highly absorbent material.

It is a still further object of the present invention to provide a dental absorbency device which comprises an elongated flat section having peripheral edges which are unobstructed to fluid flow whereby absorbing moisture, contaminants, blood, saliva, water, and/or other fluids therethrough.

In addition, it is an object of the present invention to provide a dental absorbency device comprising an internal collection reservoir having a dimensional configuration substantially complimentary to the contoured elongated shape of the flat section.

Still another object of the present invention is to provide a dental absorbency device which simplifies the absorption process and which is easy to use, economically viable, and relatively trouble free in operation.

Similarly, it is a still further object of the present invention to provide a dental absorbency device which is simple in construction and efficient in operation.

Consistent with the foregoing objects, and in accordance with the invention as embodied and broadly described herein, a dental absorbency device comprises a flat section comprising a single sheet of a highly absorbent material having a contoured elongated shape preferably sized to fit comfortably within a human mouth for the purpose of absorbing moisture, contaminants, blood, saliva, water, and/ or other fluids at an operative field. In preferred design, the flat section may be formed having an upper surface, a lower surface, and peripheral edges which are unobstructed to fluid flow so as to provide a means for encouraging the absorption of fluids therethrough. The upper surface is preferably formed having an impervious, non-absorbent coating that resists slippage of the elongated flat section when disposed within the mouth of a patient. Structurally, the upper surface of the flat section includes at least one porous opening for absorbing fluids therethrough, whereas in contrast, the lower surface provides a means For absorbing fluids through its entire external surface area. A collection reservoir is preferably disposed between the upper and lower surfaces of the elongated flat section and functions to provide a means for retaining the collected fluids therein.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF THE PREFERRED EMBODIMENTS

It will be readily understood that the components of the present invention, as generally described and illustrated in the Figures herein, could be arranged and designed in a wide variety of different configurations. Thus, the following more detailed description of the embodiments of the system and method of the present invention, as represented in FIGS. 1 through 3, is not intended to limit the scope of the invention, as claimed, but it is merely representative of the presently preferred embodiments of the invention.

The presently preferred embodiments of the invention will be best understood by reference to the drawings, wherein like parts are designated by like numerals throughout.

As disclosed herein, one of the primary purposes of the present invention is to provide an absorbent device which can be utilized during medical and/or dental procedures as a means for absorbing moisture, contaminates, debris, blood, saliva, water, and/or other fluids from the operative field. In preferred design, the dental absorbency device, as generally described at 10, is preferably formed having a suitable size and anatomical configuration so as to provide a means for easy installation and positioning within the mouth of a patient. Preferably, the dental absorbency device 10 of the present invention may be placed within a patient's mouth between the gingiva and the internal mucous membrane, between the gingiva and the lining of the cheek, between the teeth and inner lining of the cheek, and/or between the gingiva and the tongue.

Figure 1:
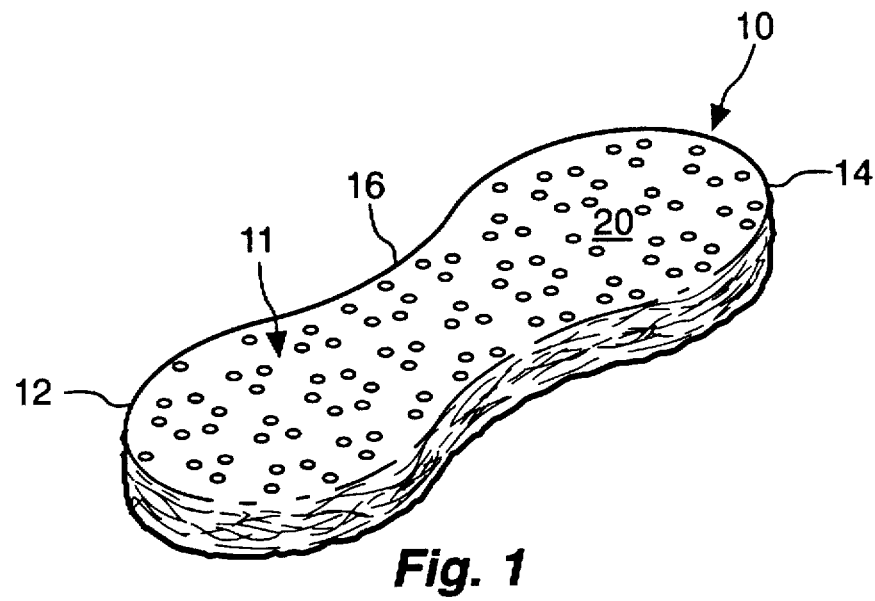
FIG. 1 is a perspective view of a dental absorbency device in accordance with one presently preferred embodiment of the present invention.
Figure 2:
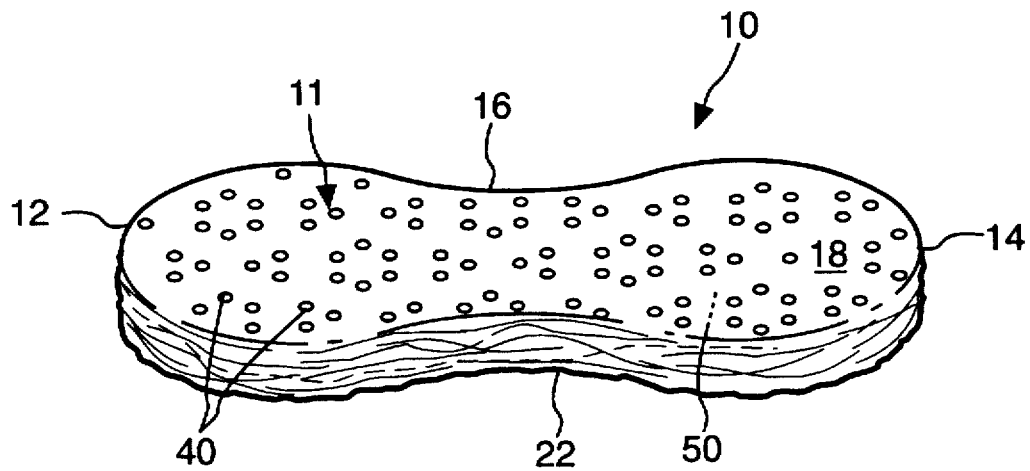
FIG. 2 is a side elevational view of one presently preferred embodiment of a dental absorbency device of the present invention.
Figure 3:
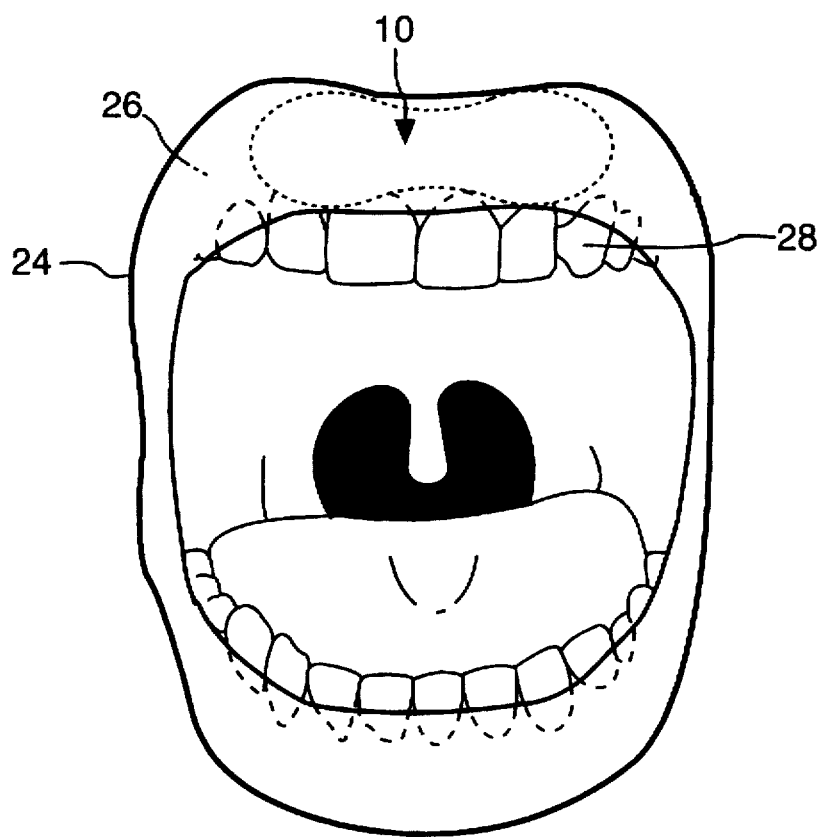
FIG. 3 is a perspective view of one presently preferred embodiment of the dental absorbency device as shown within a patient's mouth.

As best illustrated in FIGS. 1 and 2, the dental absorbency device 10 is preferably formed of at least one sheet of a flexible, highly absorbent material and formed consisting of an elongated flat section 11 having a first end 12, a second opposing end 14, and a midsection 16 operably disposed therebetween. In one presently preferred embodiment of the present invention, the dental absorbency device 10 comprises a single sheet of material having a web or mesh lattice of substantially compact, dense parallel fibers which have been subsequently gathered and consolidated to form the elongated flat section 11. For example, an absorbent material comprising the dental absorbency device 10 of at least one presently preferred embodiment may consist of a single fibrous sheet formed of cellulose fibers that have been spun-bonded together so that the orientation of the fibers in the sheet are predominantly disposed lengthwise so as to substantially stabilize the lengthwise dimension of the elongated flat section 11. In addition, the absorbent material forming the elongated flat section 11 of the dental absorbency device 10 preferably comprises a combination of synthetic polypropylene fibers and wood pulp, such as, for example, COFORM® which is currently manufactured by Kimberly-Clark.

As contemplated herein, an alternate preferred embodiment of the dental absorbency device 10 of the present invention may comprise an elongated flat section 11 formed of a porous sponge or gelatinous material for their highly absorbent qualities and characteristics. It will be readily appreciated by those skilled in the art, however, that other suitable absorbent materials which are consistent with the spirit and scope of the present invention are possible. Whereas, the absorbent materials outlined herein as comprising the dental absorbency device 10 are not intended to limit the scope of the invention, but are merely representative of one or more presently preferred embodiments of the invention.

As noted above, the elongated flat section 11 is formed having a first end 12, a second opposing end 14, and a midsection 16 disposed in connection therebetween. Preferably, the flat section 11 is formed having a substantially smooth upper surface 18 and lower surface 20 which, as used herein, means that the upper and lower surfaces 18, 20 are substantially free from roughness and projections. In one presently preferred embodiment of the dental absorbency device 10, the flat section 11 is formed having a general figure-eight configuration wherein the first end 12 and the second opposing end 14 are formed having a width greater than the width of the midsection 16, as best illustrated in FIG. 1. In this regard, the general figure-eight configuration of the elongated flat section 11 facilitates an anatomical shape which is inherently complimentary to the anterior and posterior quadrants of the normal mouth. As contemplated herein, the flat section 11 of the absorbency device 10 may be longitudinally folded in half sectionally, whereby reducing the cross-sectional width of the flat section 11 so as to facilitate installation into small, defined areas, fields, or regions within the mouth of a patient. By folding the elongated flat section 11 longitudinally, the thickness of the absorbent material comprising the dental absorbency device 10 is proportionally increased in relation thereto, thus enhancing absorption in a smaller, defined area. As should be further appreciated, the elongated flat section 11 may be folded in such a manner so as to position the first end 18 in relation to the second opposing end 20, or vice versa.

In view of the foregoing, those skilled in the art will readily recognize other possible modifications and adaptations of the shape or configuration of the absorbency device 10 which are consistent with the spirit and scope of the present invention. For example, an alternate preferred embodiment of the absorbency device 10 may be formed having a substantially rectangular, triangular, spherical, oval, tubular, elliptical, hourglass or other suitable shape or configuration. Moreover, the present invention may be utilized for purposes of a hemostatic device in cooperation with medical procedures, whereas the shape or configuration of the absorbent device 10 may vary in accordance with its designed need or use as is considered to be herein contemplated. Whereas, although the present invention is illustrated and described in connection with a general figure-eight configuration, those skilled in the art will recognize that various other geometrical configurations are likewise suitable. The use of a general figure-eight configuration is thus by way of illustration and not by way of limitation or restriction.

Disposed at the first end 12 of the flat section 11 is an annularly enlarged, generally semi-circular contoured portion forming an extension of the preferred figure-eight configuration of the dental absorbency device 10. Correspondingly, formed opposite the first end 12 at the second opposing end 14 is an annularly enlarged, generally semi-circular contoured portion which is formed substantially complimentary to the configuration of the first end 12 and comprises substantially the same dimensional width thereof. In preferred design, the first and second ends 12, 14 of the flat section 11 have a width greater than the width of the midsection 16. Similarly, the contoured anatomical shape of the elongated flat section 11 comprises a length being approximately two to four times its width. As best shown in the drawings, the midsection 16 is disposed in alignment between the first end 12 and the second end 14 of the flat section 11, whereby connecting both the first end 12 and the second end 14 of the flat section 11 in spaced apart relation therebetween.

Consistent with the absorbency of the preferably fibrous or cellulose material comprising the elongated flat section 11 of the absorbency device 10 of the present invention, an accumulation of moisture, contaminants, and/or other fluids may be absorbed by the absorbent material comprising the flat section 11 through the upper and lower surfaces 18, 20 of the elongated body, as well as through the peripheral sides 22 thereof. In particular, the peripheral sides of the dental absorbency device 10 are formed so as to be unobstructed to fluid flow whereby encouraging the absorption of moisture, contaminants, blood, saliva, water, and/or other liquids through the sides for passage into an internal collection periphery formed between the upper and lower surfaces 18, 20 of the elongated flat section 11.

In one presently preferred embodiment, the single sheet of fibrous or cellulose material forming the dental absorbency device 10 provides for an internal collection reservoir 50 having a compact density and dimensional thickness of between approximately 0.2 cm and 0.5 cm. Correspondingly, the internal collection reservoir 50 is preferably disposed within the entire internal periphery of the flat section 11 being disposed between the upper and lower surfaces 18, 20 thereof. Whereas, the accumulation of moisture, contaminants; and/or other fluids which may be absorbed through the upper surface 18, the lower surface 20, and/or the peripheral sides 22 of the flat section 11 will be generally retained within the internal collection reservoir 50 preferably defined by the elongated configuration of the flat section 11. In an alternate preferred embodiment, the single sheet of absorbent material comprising the flat section 11 may include two or more internal collection reservoir 50 which are sectionally formed within the internal periphery of the flat section 11.

In preferred construction of one presently preferred embodiment, the upper surface 18 of the elongated flat section 11 may be formed having a substantially impervious, non-absorbent coating disposed partially or entirely thereover to provide a means of resisting movement of the absorbent device 10 from a designated area when positioned within the mouth of a patient. Correspondingly, the upper surface 18 of the flat section 11 may comprise at least one small porous opening 40 formed through the impervious, non-absorbent coating to provide a means for passing moisture, contaminants, and/or other fluids through the upper surface 18 and into the internal collection reservoir 50 of the elongated flat section 11 for purposes of retaining the moisture, contaminants, and/or other fluids therein. For example, a non-permeable, melt-blown material having substantially non-wettable, hydrophobic characteristics may comprise a plurality of porous openings 40 formed therein to provide a means for absorbing moisture, contaminants, and/or other fluids therethrough and into the internal collection reservoir 50. An alternate preferred embodiment of the present invention may include an impervious, non-absorbent coating disposed partially or entirely over the external surface area of the upper surface 18 of the elongated flat section 11 which comprises no porous openings 40 formed therein, thus providing a means for retaining the absorbency device 10 of the present invention in its intended position within the mouth of the patient without facilitating absorption through the upper surface 18.

Preferably, the present invention includes a surfactant to enhance its absorbency of moisture, contaminants, blood, saliva, water, and/or other liquids. In addition, the dental absorbency device 10 may also contain a flavoring impregnated therein for use in dental procedures. Thus, in use, the flavoring agent may be gradually released during a dental procedure to create a tasteful diversion for the patient undergoing the procedure. Correspondingly, the flavor releasing substance may comprise a dehydrated water-soluble flavoring agent that may be dispersed throughout at least a portion of the absorption material forming the dental absorbency device 10.

A tab (not shown) may be incorporated into the structure of the present invention by means of comprising an attachment which can be fastened or formed as a removable or unitary part of the upper surface 18 or the lower surface 20 of the flat section 11 to assist in the placement of the dental absorbency device 10 at its intended position. It will be readily appreciated by those skilled in the art, however, that other suitable fasteners or positioning members are possible. It is intended, therefore, that the example provided herein be viewed as exemplary of the principles of the present invention, and not as restrictive to a particular structure for implementing those principles In one presently preferred method or technique of the present invention, the absorbency device 10 may be introduced into the mouth of a patient and positioned in an area contiguous to the performance of a dental procedure such as, for example, between the gingiva and the internal mucous membrane, between the gingiva and the lining of the cheek, between the teeth and the inner lining of the cheek, and/or between the gingiva and the tongue. Moisture, contaminants, debris, saliva, blood, water, and/or other fluids may be readily absorbed into the elongated body of the flat section 11 through the upper surface 18, the lower surface 20, and/or the peripheral sides 22 thereof and retained within the internal collection reservoir 50. Accordingly, the dental absorbency device 10 can be removed from the mouth of the patient after a dental procedure having the collected fluids disposed therein.

From the foregoing, it is anticipated that the shape or configuration of the dental absorbency device 10 of the present invention comprises a sufficient dimensional size to provide a flat section 11 that generally extends across one or more teeth of a patient or a portion of the gingiva to provide a means for absorbing moisture, contaminants, and/or other fluids in the operative field. In one presently preferred technique or method of use of the dental absorbency device 10 of the present invention, the mouth of a patient may be exposed in an open posture showing the placement of one presently preferred embodiment of the dental absorbency device 10 disposed within the anterior upper quadrant and, more specifically, the frenum area of the patient's mouth between the gingiva 26 supporting the front teeth 28 and the upper lip 24, as best illustrated in FIG. 3. As will be appreciated by those skilled in the art, the dental absorbency device 10 preferably comprises various anatomical shapes which may be utilized in various work areas, fields, or quadrants of the mouth of a patient to provide a means for absorbing moisture, contaminants, and/or other fluids to maintain the operative working area, field, or quadrant contiguous the absorbency device 10 sufficiently dry during a dental procedure.

As contemplated herein, one or more dental absorbency devices 10 of the present invention may be introduced at various positions within the mouth of a patient. In this regard, different shapes or configurations of the dental absorbency device 10 may be used in cooperation, one with the other, to enhance the inherent functionality of the dental absorbency devices 10.

From the above discussion, it will be appreciated that one presently preferred embodiment of the dental absorbency device 10 of the present invention comprises a single sheet of flexible, highly absorbent material providing a means for absorbing moisture, contaminants, blood, saliva, water, and/or other liquids through an upper surface 18, a lower surface 20, and peripheral sides 22 of an elongated flat section 11 and into an internal collection reservoir 50 thereof. In particular, the peripheral sides 22 of the absorbency device 10 are formed so as to be unobstructed thus providing a means for encouraging absorption through the sides and into the internal collection reservoir 50, thus increasing the overall rate of absorbency of the present invention.

The present invention further provides an absorbency device 10 having a single sheet of absorbent material which may be formed in a complimentary anatomical configuration for positioning within the mouth of a patient so as to provide a relative fit contiguous an operative field that is generally flatter in dimensional shape whereby displacing less area between the gingiva and the inner lining of the cheek, between the teeth and the inner lining of the cheek, between the teeth and the lip, and/or between the gingiva and the tongue.

Unlike known prior art devices, due to the particular characteristics of the absorbent material preferably comprising the dental absorbency device 10, there is no fiber residue remaining after utilization of the present Invention. In addition, the dental absorbency device 10 of the present invention may be used in combination with various dental apparatus and methods. For example, the present invention is useful when arranged below a conventional rubber dam which is installed in the mouth of a patient so as to cover an area with a tooth to be worked on and fitted therethrough. Similarly, the dental absorbency device 10 may be incorporated in several dental procedures including, but not limited to, the cutting of an amalgam preparation; crown and bridge preparation; surgical procedures; cementing of crowns, bridges, or the like; placement of amalgam or composite fillings; making of an impression of one or more teeth; and other isolated procedures. From the foregoing, it should be apparent that the dental absorbency device 10 preferably extends across one or more teeth of a patient providing for an absorption of liquid on either side of the contiguous tooth or teeth as a barrier to liquid flowing or otherwise passing onto the work surface whereon the dental procedure is being performed.

From the above discussion, it will be appreciated that the present invention provides a novel dental absorbency device having a contoured elongated shape for fitting comfortably and conveniently within the mouth of a patient in order to provide a means for absorbing moisture, contaminants, blood, saliva, water, and/or other fluids from an operative field. Additionally, the present invention is formed of a single sheet of a flexible, highly absorbent material which comprises an elongated flat section having peripheral edges that are unobstructed to fluid flow thereby providing a means for absorbing moisture, contaminants, blood, saliva, water, and/or other fluids therethrough in addition to the upper and lower surfaces.

Unlike the prior art, the present invention comprises an internal collection reservoir having a dimensional configuration substantially complimentary to the contoured elongated shape of the flat section. The present invention further provides a dental absorbency device which simplifies the absorption process and which is relatively trouble free in operation, economically viable, simple in construction, and efficient in operation.

Consistent with the foregoing, the present invention may be embodied in other specific forms without departing from its spirit or essential characteristics The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A dental absorbency device for collecting fluids, comprising:

a flat section comprising a single sheet of a highly absorbent material, said flat section including a first end, a second opposing end, and a midsection disposed in connection therebetween, said flat section formed having a contoured elongated shape sized to fit comfortably within a human mouth;

an upper surface of said flat section, said upper surface comprising means for resisting slippage of the flat section, said upper surface having at least one porous opening formed therein for absorbing said fluids therethrough;

a lower surface of said flat section providing means for absorbing said fluids therethrough;

edges formed along an outer periphery of said flat section, said peripheral edges being unobstructed to fluid flow wherein providing means for absorbing said fluids therethrough; and a collection reservoir disposed between said upper surface and said lower surface of said flat section, said collection reservoir providing means for retaining said fluids therein.

2. A dental absorbency device as defined in claim 1 further comprising a surfactant.

3. A dental absorbency device as defined in claim 1 further comprising a flavoring agent.

4. A dental absorbency device as defined in claim 1 wherein said sheet of absorbent material comprises a dimensional thickness of between approximately 0.2 cm and 0.5 cm.

5. A dental absorbency device as defined in claim 1 wherein said sheet of absorbent material comprises a lattice of substantially compact, dense parallel fibers.

6. A dental absorbency device as defined in claim 5 wherein said absorbent material includes a combination of synthetic polypropylene fibers and wood pulp.

7. A dental absorbency device as defined in claim 1 wherein said absorbent material comprises a single fibrous sheet of cellulose fibers being spun-bond together, wherein said fibers being predominantly disposed lengthwise.

8. A dental absorbency device as defined in claim 1 wherein said flat section comprises a length approximately two to four times its width.

9. A dental absorbency device as defined in claim 1 wherein said first and second ends comprise a width being greater than a width at said midsection.

10. A dental absorbency device as defined in claim 1 wherein said means for resisting slippage comprises an impervious, non-absorbent coating.

11. A dental absorbency device as defined in claim 1 wherein said upper and lower surfaces are formed having an exterior surface being substantially smooth.

12. A dental absorbency device as defined in claim 1 wherein said peripheral edges slope uniformly outward from said midsection to said first and second ends.

13. A dental absorbency device as defined in claim 1 wherein said collection reservoir comprises a configuration being substantially complimentary to said contoured elongated shape of said flat section.

14. A dental absorbency device for collecting fluids, comprising:
a flat section comprising a single sheet of a highly absorbent material, said flat section including a first end, a second opposing end, and a midsection disposed in connection therebetween, said flat section formed having a contoured elongated shape sized to fit comfortably within a human mouth, said elongated shape comprising a length approximately two to four times its width and a width at said first and second ends being greater than a width at said midsection;

an upper surface of said flat section, said upper surface comprising an impervious, non-absorbent coating providing a means for resisting slippage of the flat section, said upper surface including a plurality of porous openings formed therein for absorbing said fluids therethrough;

a lower surface of said flat section having a configuration complimentary to said upper section, said lower surface providing means for absorbing said fluids therethrough;

edges formed along an outer periphery of said flat section, said peripheral edges being unobstructed to fluid flow wherein providing means for absorbing said fluids therethrough; and a collection reservoir disposed between said upper surface and said lower surface of said flat section for retaining said fluids therein, said collection reservoir having an elongated shape substantially complimentary to said elongated shape of said flat section.

15. A dental absorbency device as defined in claim 14 further comprising a flavoring agent.

16. A dental absorbency device as defined in claim 14 wherein said sheet of absorbent material includes a combination of synthetic polypropylene fibers and wood pulp.

17. A dental absorbency device as defined in claim 14 wherein said sheet of absorbent material comprises a dimensional thickness of between approximately 0.2 cm and 0.5 cm.

18. A dental absorbency device as defined in claim 14 wherein said peripheral edges slope uniformly outward from said midsection to said first and second ends.

19. A dental absorbency device for collecting fluids, comprising:
a flat section comprising a single sheet of a highly absorbent material including a combination of synthetic polypropylene fibers and wood pulp and having a dimensional thickness of between approximately 0.2 cm and 0.5 cm., said flat section including a first end, a second opposing end, and a midsection disposed in connection therebetween, said flat section formed having a contoured elongated shape sized to fit comfortably within a human mouth, said elongated shape comprising a length being approximately two to four times its width and a width at said first and second ends being greater than at said midsection;

an upper surface of said flat section providing a substantially smooth surface, said upper surface having an impervious, non-absorbent coating for resisting slippage of the flat section, said upper surface further comprising a plurality of porous openings formed therein for absorbing said fluids therethrough;

a lower surface of said flat section having a configuration complimentary to said upper section and providing a substantially smooth surface, said lower surface providing means for absorbing said fluids therethrough;

edges formed along an outer periphery of said flat section, said peripheral edges sloping uniformly outward from said midsection to said first and second ends and being unobstructed to fluid flow wherein providing means for absorbing said fluids therethrough; and a collection reservoir disposed between said upper surface and said lower surface of said flat section for retaining said fluids therein, said collection reservoir having an elongated shape substantially complimentary to said elongated shape of said flat section and said dimensional thickness of said absorbent material.

* * * * *